(12) United States Patent
Adams

(10) Patent No.: US 7,338,495 B2
(45) Date of Patent: Mar. 4, 2008

(54) ANGLED TISSUE CUTTING INSTRUMENTS HAVING FLEXIBLE INNER TUBULAR MEMBERS OF TUBE AND SLEEVE CONSTRUCTION

(75) Inventor: Kenneth M. Adams, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 742 days.

(21) Appl. No.: 10/689,627

(22) Filed: Oct. 22, 2003

(65) Prior Publication Data

US 2005/0090848 A1 Apr. 28, 2005

(51) Int. Cl.
*A61B 17/32* (2006.01)

(52) U.S. Cl. .................. 606/79; 606/180
(58) Field of Classification Search ........... 606/167, 606/170, 180; 464/78
See application file for complete search history.

(56) References Cited

U.S. PATENT DOCUMENTS

| | | | |
|---|---|---|---|
| 177,490 A | 5/1876 | Fones et al. | |
| 4,203,444 A | 5/1980 | Bonnell et al. | |
| 4,445,509 A | 5/1984 | Auth | |
| 4,466,429 A | 8/1984 | Loscher et al. | |
| 4,646,738 A * | 3/1987 | Trott | 606/170 |
| 5,152,744 A * | 10/1992 | Krause et al. | 604/22 |
| 5,286,253 A * | 2/1994 | Fucci | 604/22 |
| 5,314,438 A | 5/1994 | Shturman | |
| 5,322,505 A | 6/1994 | Krause et al. | |
| 5,350,797 A * | 9/1994 | Stephan et al. | 525/28 |
| 5,383,889 A * | 1/1995 | Warner et al. | 606/192 |
| 5,465,733 A * | 11/1995 | Hinohara et al. | 600/585 |
| 5,529,580 A | 6/1996 | Kusunoki et al. | |
| 5,658,264 A * | 8/1997 | Samson | 604/264 |
| 5,690,660 A * | 11/1997 | Kauker et al. | 606/180 |
| 5,707,350 A * | 1/1998 | Krause et al. | 604/22 |
| 5,755,731 A * | 5/1998 | Grinberg | 606/180 |
| 5,762,069 A * | 6/1998 | Kelleher et al. | 600/564 |
| 5,807,241 A | 9/1998 | Heimberger | |
| 5,833,692 A * | 11/1998 | Cesarini et al. | 606/79 |
| 5,851,208 A * | 12/1998 | Trott | 606/80 |
| 5,908,381 A * | 6/1999 | Aznoian et al. | 600/104 |
| 5,922,003 A * | 7/1999 | Anctil et al. | 606/170 |
| 6,053,922 A * | 4/2000 | Krause et al. | 606/80 |
| 6,217,595 B1 | 4/2001 | Shturman et al. | |
| 6,290,709 B1 * | 9/2001 | Ellis et al. | 606/167 |
| 6,312,438 B1 * | 11/2001 | Adams | 606/159 |
| 6,533,749 B1 | 3/2003 | Mitusina et al. | |
| 6,682,493 B2 * | 1/2004 | Mirigian | 600/585 |
| 6,702,828 B2 * | 3/2004 | Whayne | 606/153 |

* cited by examiner

*Primary Examiner*—Glenn K. Dawson

(57) ABSTRACT

An angled tissue cutting instrument comprises an angled outer tubular member rotatably receiving a flexible inner tubular member. The inner member has a flexible region in correspondence with an angle of the outer member. The flexible region comprises a helically cut length portion of an elongate tubular body of the inner member and a continuous solid flexible surface secured to an outer surface of the body along the helically cut length portion. A method of fabricating a flexible inner tubular member involves forming a helical cut through the solid wall of a length portion of a tubular body and securing a continuous solid flexible surface to the outer surface of the body along the helically cut length portion to form a flexible region.

16 Claims, 4 Drawing Sheets

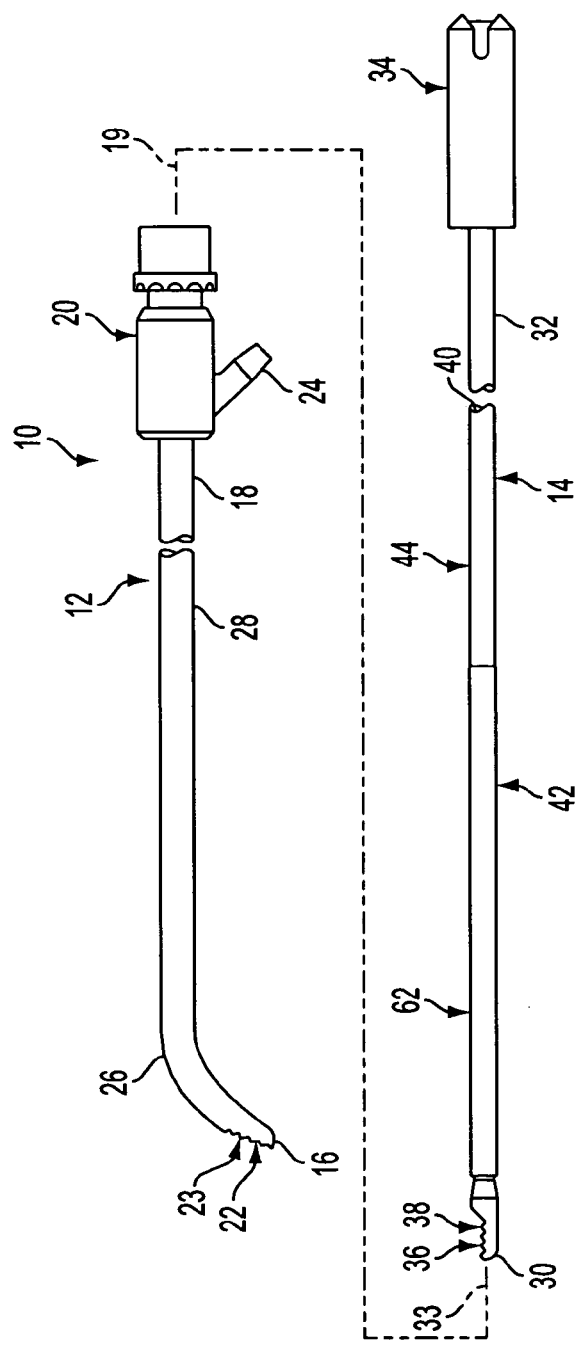
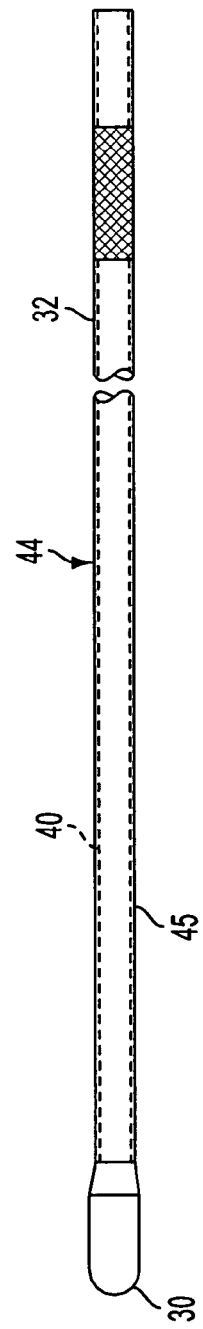
FIG. 1
FIG. 2

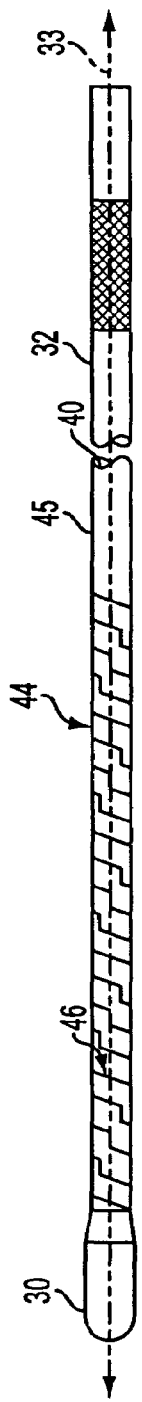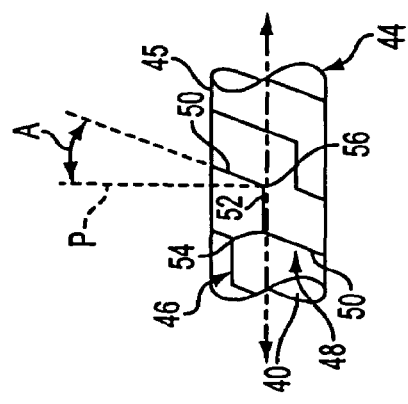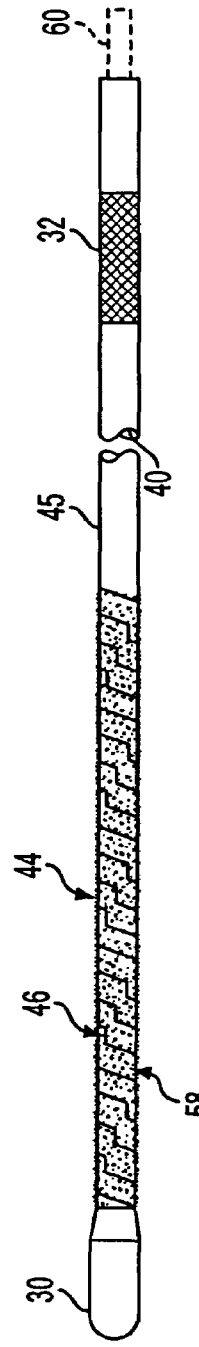
FIG. 3
FIG. 4
FIG. 5

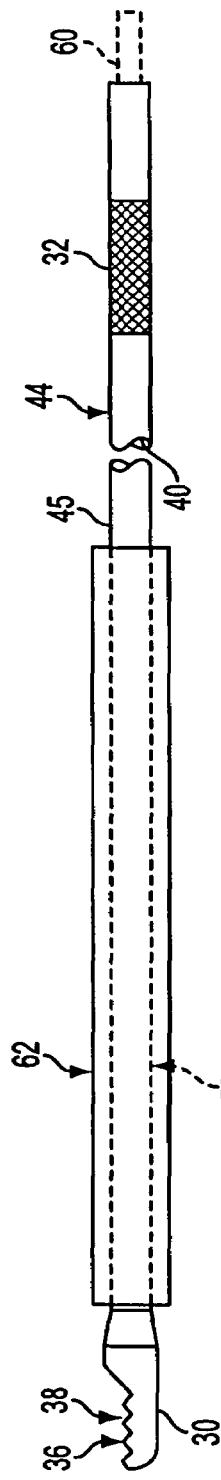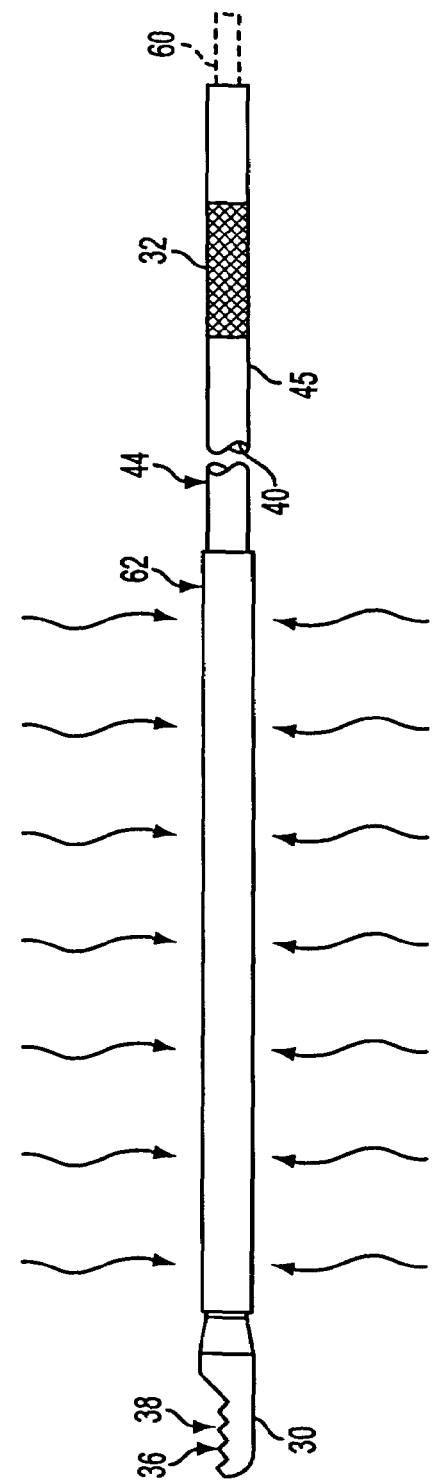

ANGLED TISSUE CUTTING INSTRUMENTS HAVING FLEXIBLE INNER TUBULAR MEMBERS OF TUBE AND SLEEVE CONSTRUCTION

BACKGROUND OF THE INVENTION

1. Field of the Invention

The present invention relates generally to tissue cutting instruments having an elongate inner member rotatably disposed in an elongate outer tubular member to cut anatomical tissue and, more particularly, to angled tissue cutting instruments and methods of fabricating angled tissue cutting instruments having an elongate flexible inner tubular member rotatably disposed in an elongate angled outer tubular member.

2. Discussion of the Related Art

Surgical cutting instruments in which an elongate inner member is rotated within an elongate outer tubular member have become well accepted in surgical procedures where access to a cutting site in a patient's body is gained via a narrow or small size natural or surgically created anatomical opening or passage establishing communication with the cutting site from externally of the patient's body. Typically, the outer tubular member includes a distal end with an opening defining a cutting port or window, and the inner member includes a distal end carrying a cutting configuration exposed by or from the cutting port for engaging anatomical tissue at the cutting site. Proximal ends of the inner and outer members ordinarily include hubs which attach to a powered handpiece disposed externally of the patient's body and having a motor for rotating the inner member relative to and within the outer member. The cutting configuration of the inner member can have various configurations depending upon the surgical procedure to be performed, the type of tissue to be cut and/or the desired cutting action. The opening in the distal end of the outer member may be suitably configured to cooperate with the particular cutting configuration of the inner member to cut anatomical tissue. Often the inner member is tubular and has an aspiration port at its distal end communicating with the lumen of the inner tube so that material, including loose tissue resulting from a cutting procedure, can be aspirated from the cutting site through the aspiration port and lumen of the inner member. Many tissue cutting instruments are designed to allow irrigating fluid to flow along the instruments for discharge at the cutting site, and some tissue cutting instruments are designed for flow of irrigating fluid between the outer and inner members. It is advantageous in tissue cutting instruments for the direction of rotation of the inner member to be reversible during operation for operation of the instruments in both forward and reverse rotational directions. An example of a rotary tissue cutting instrument of the aforementioned type is described in U.S. Pat. No. 4,203,444 to Bonnell et al for use in performing arthroscopic knee surgery.

Many tissue cutting instruments are straight, with longitudinally or axially straight inner and outer members as represented by the Bonnell et al patent. In straight tissue cutting instruments, it is typical for the outer tubular member to comprise an outer tube and for the inner tubular member to comprise an inner tube having an outer diameter for being accommodated in the inner diameter of the outer tube while allowing the inner tube to rotate within the outer tube. Typically, there is a small annular gap or clearance between the outer diameter of the inner tube and the inner diameter of the outer tube, and irrigating fluid may flow along the irrigation channel defined by this gap or clearance for discharge through the cutting port. The lumen of the inner tube defines the aspiration passage in communication with the aspiration port at the distal end of the inner tube and through which material is aspirated when suction is produced in the lumen of the inner tube. Since an elongate body of the straight inner tube is normally of unbroken solid wall construction, there are no openings through the wall of the body of the inner tube through which suction in the aspiration passage may be lost and/or through which irrigating fluid may be drawn into the aspiration passage.

In many surgical procedures, it is advantageous for the tissue cutting instruments to be non-straight or angled to access cutting sites which are not accessible or are more difficult to access with straight tissue cutting instruments. Angled tissue cutting instruments normally comprise an elongate angled outer tubular member and an elongate flexible inner tubular member which conforms to the angled configuration of the outer member while being rotatable therein. The angled configuration of the outer member can be formed by various angles, bends or curves, as limited by the ability of the flexible inner tubular member to bend. As with straight tissue cutting instruments, irrigating fluid may flow through an irrigation channel between the angled outer tubular member and the flexible inner tubular member, and aspiration may be conducted through an aspiration passage of the flexible inner tubular member.

The flexible inner tubular members of many angled tissue cutting instruments utilize spirally or helically wound coils or springs to transmit torque to rotate the cutting configuration when the inner members are rotated within the outer members. Flexible inner members that employ a single spirally or helically wound coil to impart flexibility while transmitting torque are represented by U.S. Pat. No. 4,466,429 to Loscher et al and U.S. Pat. No. 4,445,509 to Auth. A single coil tends to unwind when rotated in a direction opposite its winding so that torque can only be transmitted efficiently in one rotational direction. Accordingly, angled tissue cutting instruments utilizing this type of flexible inner member cannot be operated in both forward and reverse rotational directions.

Flexible inner tubular members having a plurality of coaxial spirally or helically wound coils disposed one on top of the other and wound in alternating opposite directions relative to one another have been used in angled tissue cutting instruments to transmit torque in both rotational directions. U.S. Pat. No. 4,646,738 to Trott describes an angled tissue cutting instrument in which the flexible inner tubular member comprises separate distal and proximal end portions and a composite spiral interposed between the distal and proximal end portions to allow the inner tubular member to bend. The composite spiral is similar to the flexible shaft disclosed in U.S. Pat. No. 177,490 to Fones et al and is made up of an inner spiral, a middle spiral and an outer spiral arranged one on top of the other with their windings alternating in direction. The distal and proximal end portions include reduced diameter neck portions which are telescopically received within opposite ends of the inner spiral to facilitate welding of the distal and proximal end portions to opposite ends of the composite spiral. Each spiral adds material and labor costs to the flexible inner tubular member and, therefore, to the angled tissue cutting instrument. Another disadvantage of the flexible inner tubular member used in the Trott instrument is that the neck portions tend to stiffen the composite spiral in the vicinity of the cutting tip thereby preventing the inner member from bending adjacent the cutting tip. In addition, it is possible for the separate components to become detached from one another during use such that torque can no longer be effectively transmitted to the cutting configuration. Angled tissue cutting instruments in which the flexible inner tubular member is like that disclosed in the Trott patent are described in U.S. Pat. No. 5,286,253 to Fucci and U.S. Pat. No. 5,529,580 to Kusunoki et al.

U.S. Pat. No. 5,314,438 to Shturman and U.S. Pat. No. 6,217,595 to Shturman et al relate to a flexible drive shaft comprising inner and outer oppositely wound helical wire layers along the entire length of the drive shaft. The drive shaft of the Shturman patent is referred to in the Shturman et al patent as being difficult and time-consuming to manufacture. The drive shaft of the Shturman et al patent has its outer helical layer made up of a single wire and its inner helical layer made up of a plurality of wires, which must all be wound around a forming mandrel so that the drive shaft requires many parts and is still difficult and time-consuming to manufacture. Flexible shafts or tubular members comprising two layers of helical windings or coils have many of the same disadvantages as flexible tubular members that have three helical windings or coils.

Another disadvantage associated with the use of helical coils or springs to transmit torque while imparting flexibility is that spaces or gaps between the coils may be presented along the body of the flexible inner tubular member which allow suction in the lumen or aspiration passage of the inner tubular member to be dissipated such that less suction is applied at the aspiration port for reduced aspiration efficiency. A weakened suction force or vacuum in the aspiration passage and/or at the aspiration port may lead to clogging or jamming of the tissue cutting instrument due to tissue build-up. Clogging or jamming of tissue cutting instruments due to tissue build-up undesirably leads to the need for frequent cleaning or substitution of the instruments during use, which is time consuming and increases the duration of the surgical procedure to the detriment of the patient and the surgeon. Loss of irrigation efficiency is another problem where spaces are presented between the coils, since irrigating fluid flowing between the outer and inner members may be drawn through the spaces into the aspiration passage. An additional drawback of helical coils or springs is the tendency of the coils or springs to require tightening or preloading. Furthermore, coils or springs have a tendency under certain loading conditions to relax or unwind, and thus expand, thereby increasing the possibility of the inner member binding within the outer member. Relaxation of the coils or springs also makes it more likely that sizable spaces or gaps will be presented between the coils, especially on bending, through which suction in the lumen of the inner member may be lost and/or through which irrigating fluid flowing between the inner and outer members may be drawn into the inner member lumen.

U.S. Pat. No. 5,922,003 to Anctil et al relates to an angled tissue cutting instrument and to a method of fabricating an angled tissue cutting instrument in which the flexible inner tubular member has a flexible region interposed between a drive shaft and a cutting tip. The flexible region includes a flexible polymeric tube having ends that receive necks of the drive shaft and cutting tip, respectively. A collar of heat shrink tubing is disposed over each end of the tube. When heat is applied, the collars shrink and the polymeric material is caused to flow into slots in the necks to form a mechanical joint. The heat shrunk tubing may be removed after the polymeric material has cured. Counter wound wires embedded in the polymeric material assist in transmitting torque in forward and reverse rotational directions.

Another approach to flexible inner tubular members of angled tissue cutting instruments has involved forming relief apertures or slots through the walls of solid inner tubes to impart flexibility to the inner tubes as represented by U.S. Pat. No. 5,152,744 and U.S. Pat. No. 5,322,505 to Krause et al. In the angled tissue cutting instruments described in the aforementioned Krause et al patents, the inner tubes have discrete, unconnected apertures or slots formed therein such that torque transmission is limited. Also, the slots present spaces through which fluid can flow to and from the lumen of the inner tube.

U.S. Pat. No. 5,807,241 to Heimberger discloses a flexible tube particularly useful as a shank for a flexible endoscope. The flexible tube is formed by cutting a gap in a closed path in a longitudinally straight solid tube to form interlocking but completely materially or physically separated tube sections that allow the tube to bend axially. The flexible tube may not be well suited for use as a rotatable inner tubular member of a surgical cutting instrument since its torque capabilities may be limited to relatively low single direction and bidirectional rotational speeds. Additionally, it is possible for the individual tube sections to disconnect or become detached when the tube is bent. Spaces are presented between the individual tube sections allowing the exchange of fluid between the outside and the inside of the tube.

Angled tissue cutting instruments having inner tubes with continuous helical cuts therein to impart flexibility are illustrated by U.S. Pat. No. 6,053,922 to Krause et al, U.S. Pat. No. 6,312,438 B1 to Adams and U.S. Pat. No. 6,533,749 B1 to Mitusina et al. In the angled tissue cutting instruments disclosed by Krause et al '922, no additional layer of material is secured over the helically cut inner tube. Accordingly, the instrument may be suitable for transmitting torque in one direction only and may be of limited torsional strength, as well as the helical cut presenting a space through the wall of the inner tube through which fluid may flow. The angled tissue cutting instruments described in the Adams and Mitusina et al patents have flexible inner tubular members including flexible regions formed by a helical cut in an inner tube and two spiral wrap layers disposed over the helical cut in the inner tube one on top of the other in alternating directions. The instruments disclosed in the Adams and Mitusina et al patents overcome the primary disadvantages of wound helical coils or springs and can effectively transmit torque in both rotational directions at relatively high rotational speeds with minimal wind-up and with the structurally interconnected inner tube eliminating the problems of disconnection or detachment of the inner tube. The use of multiple spiral wrap layers over the helical cut reduces but does not eliminate the possibility of suction being lost from the lumen of the inner tube and/or irrigating fluid entering into the lumen of the inner tube since the helical cut and spiral wraps still present spaces for fluid flow between the outside and the inside of the tubular member. The use of a helically cut inner tube achieves a high degree of bendability and allows flexibility to be imparted to the inner tube adjacent the cutting configuration. However, each spiral wrap layer adds material and labor costs to the flexible inner tubular member and, therefore, to the angled tissue cutting instrument.

It would be desirable to provide an alternative construction for the flexible inner tubular members of angled tissue cutting instruments wherein the flexible inner tubular members retain the benefits of utilizing a helically cut inner tube and allowing torque transmission in forward and reverse rotational directions, while replicating a solid wall inner tubular member construction for increased aspiration and irrigation efficiencies and reduced risk of clogging, reducing wind-up, providing increased structural strength, and reducing the labor and materials needed to fabricate the flexible inner tubular members of various diametric sizes of angled tissue cutting instruments having angled outer members with angles of various magnitudes, radii of curvature and directions.

SUMMARY OF THE INVENTION

The present invention is generally characterized in an angled tissue cutting instrument comprising an elongate angled outer tubular member and an elongate flexible inner tubular member rotatably disposed within the outer tubular member to transmit torque in forward and reverse rotational directions. The outer tubular member includes a proximal end, a distal end, a bend between the proximal end and the distal end, and an opening at the distal end defining a cutting port in communication with the lumen of the outer tubular member. The inner tubular member comprises a proximal end, a distal end, an elongate tubular body between the proximal end and the distal end of the inner tubular member, and a cutting configuration at the distal end of the inner tubular member for exposure by the cutting port to cut anatomical tissue when the inner tubular member is rotated within the outer tubular member. A continuous helical cut is prior to the helical cut being formed therein. The helical cut is formed in the tubular body at a helix angle in a first direction about the tubular body to impart flexibility along the length portion by which the inner tubular member conforms to the angled outer tubular member while being rotated within the angled outer tubular member. A continuous solid flexible surface is secured to an outer surface of the tubular body. A flexible region of the inner tubular member comprises the helically cut length portion of the tubular body and the flexible surface secured to the outer surface of the tubular body along the helically cut length portion. The flexible region is in correspondence with the bend in the angled outer tubular member such that the flexible region is disposed within and conforms to the bend while transmitting torque to the cutting configuration when the inner tubular member is rotated relative to and within the outer tubular member in the forward and reverse rotational directions. The lumen of the tubular body defines an aspiration passage through the flexible inner tubular member, and an aspiration port at the distal end of the inner tubular member is in communication with the aspiration passage. An irrigation channel is defined between the inner diameter of the outer tubular member and the outer diameter of the inner tubular member. The flexible region replicates a solid wall tubular construction such that suction in the aspiration passage is not lost through the wall of the flexible region and irrigating fluid in the irrigating channel does not enter the aspiration passage through the wall of the flexible region.

The flexible surface may comprise a heat shrunk sleeve disposed over the helically cut length portion. The flexible region may further include a layer of adhesive between the sleeve and the outer surface of the tubular body by which the sleeve is secured to the tubular body. The helical cut may be formed in the tubular body in a stepped pattern comprising repeating interconnected steps. Each step comprises a transverse cut segment extending transverse to the length of the tubular body at the helix angle in the first direction and a longitudinal cut segment extending from the transverse cut segment along the length of the tubular body. The transverse cut segment meets the longitudinal cut segment at an outside corner forming a step configuration. The longitudinal cut segment extends from the transverse cut segment at the outside corner to an inside corner at which the longitudinal cut segment meets the transverse cut segment of the next step. The steps repeat at about 120 degree rotational intervals about a central longitudinal axis of the tubular body. In a preferred embodiment, the helix angle is 20 degrees. The helical cut tightens as the inner tubular member is rotated relative to and within the outer tubular member in a forward rotational direction. The flexible surface prevents the tubular body from unwinding when the inner tubular member is rotated in a reverse rotational direction such that the inner tubular member transmits torque to the cutting configuration in both forward and reverse rotational directions. The bond between the flexible surface and the tubular body reduces wind-up in that clockwise and counterclockwise movements are restricted.

The present invention is further characterized in a method of fabricating an angled tissue cutting instrument and, in particular, the flexible inner tubular member of an angled tissue cutting instrument. The method involves forming a continuous helical cut along a solid wall length portion of an elongate tubular body at a helix angle in a first direction about the tubular body to impart flexibility along the length portion, and securing a continuous solid flexible surface to an outer surface of the tubular body along the length portion to form a flexible region. The tubular body is inserted for rotation within an angled outer tubular member with the flexible region disposed within a bend in the outer tubular member and a cutting configuration carried at a distal end of the tubular body exposed by a cutting port in a distal end of the outer tubular member. The step of securing may involve positioning a heat shrinkable sleeve over the helically cut length portion of the tubular body with an adhesive disposed between the sleeve and the outer surface of the tubular body, and applying heat to shrink the sleeve diametrically over the tubular body.

Other objects and advantages of the present invention will become apparent from the following description of preferred embodiments taken in conjunction with the accompanying drawings, wherein like parts in each of the several figures are identified by the same reference numerals.

BRIEF DESCRIPTION OF THE DRAWINGS

FIG. 1 is an exploded broken side view of an angled tissue cutting instrument according to the present invention.

FIG. 2 is a broken side view of an inner tube of the flexible inner tubular member of the angled tissue cutting instrument of the present invention.

FIG. 3 is a broken side view of the inner tube with a helical cut formed in an elongate tubular body of the inner tube to impart flexibility along a length portion of the tubular body.

FIG. 4 is an enlarged detail view depicting a stepped pattern for the helical cut in the tubular body.

FIG. 5 is a broken side view of the inner tube with an adhesive disposed over the helically cut length portion of the tubular body.

FIG. 6 is a broken side view of the inner tube depicting a heat shrinkable sleeve positioned over the helically cut length portion of the tubular body.

FIG. 7 is a broken side view illustrating the application of heat to shrink the sleeve diametrically over the tubular body to form the flexible inner tubular member.

DETAILED DESCRIPTION OF THE PREFERRED EMBODIMENTS

Figure 8:
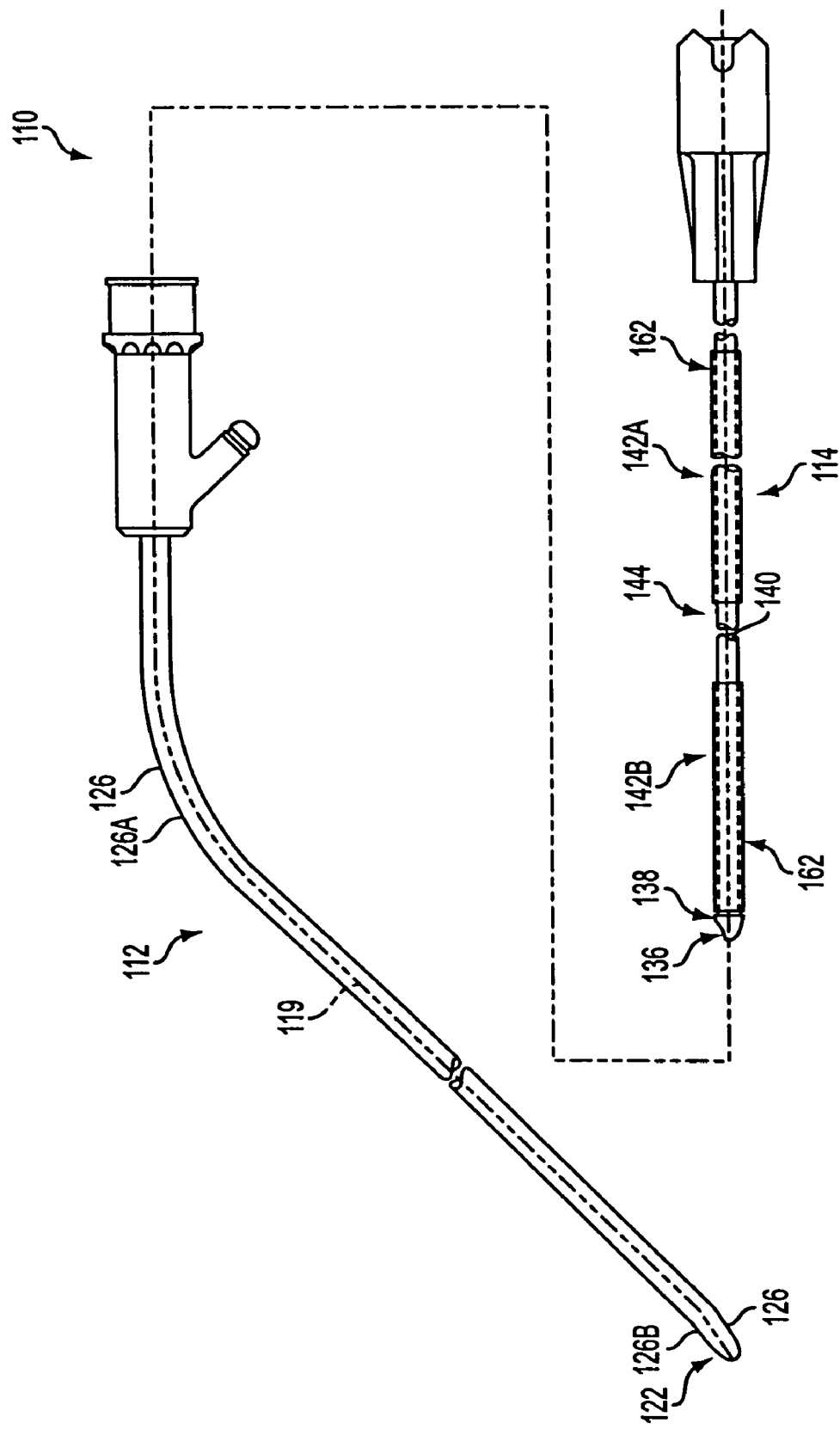
FIG. 8 is an exploded broken side view of an alternative angled tissue cutting instrument according to the present invention.

An angled tissue cutting instrument 10 according to the present invention is illustrated in FIG. 1 and comprises an elongate angled outer tubular member 12 and an elongate flexible inner tubular member 14 for being rotatably disposed in angled outer tubular member 12. The angled outer tubular member 12 is typically made of stainless steel and includes a distal end 16, a proximal end 18 and a central longitudinal axis 19 that follows a non-straight or angled longitudinal path. The proximal end 18 is typically attached to an outer member hub 20, which may be made of plastic. An opening is formed in the distal end 16 and defines a cutting port or window 22 providing communication with the lumen of the outer tubular member 12 from externally of distal end 16. The cutting port 22 can have various configurations and may be circumscribed by a peripheral edge. The peripheral edge that circumscribes the cutting port 22 can be a non-cutting edge or a cutting edge as depicted for outer tubular member 12, which has a peripheral cutting edge 23 circumscribing the cutting port 22. The cutting edge 23 can have various configurations to cut anatomical tissue including a series of cutting teeth on opposite sides of axis 19 as shown for cutting edge 23. The outer member hub 20 may have a connector 24 in communication with the lumen of the angled outer tubular member 12 by which irrigating fluid may be supplied to the lumen of the outer tubular member 12 as described further below.

Angled outer tubular member 12 has one or more bends, curves or angles 26, each of which may be of various magnitudes and radii of curvature and may extend in various directions at various locations along the length of the outer tubular member 12. Angled outer tubular member 12 has a single bend 26 and includes a straight proximal length portion 28 extending distally from outer member hub 20 to the bend 26 which is adjacent, near or close to the distal end 16. The central longitudinal axis 19 of the outer tubular member 12 is contained in a plane, with the bend 26 extending downwardly in this plane from the proximal length portion 28 looking at FIG. 1. However, it should be appreciated that the central longitudinal axis 19 of the outer tubular member 12 does not have to lie in or be contained in a plane and that the bend 26 may extend upwardly, downwardly or laterally from the proximal length portion 28.

The flexible inner tubular member 14 includes a distal end 30, a proximal end 32 and a central longitudinal axis 33 of variable configuration due to flexibility of the inner tubular member 14. The proximal end 32 is typically attached to an inner member hub 34, which may be made of plastic. The distal end 30 carries a cutting configuration 36 that may have various configurations to cut anatomical tissue. An opening is formed through the distal end 30 and defines an aspiration or suction port 38 in communication with an aspiration or suction passage defined by the lumen 40 of the flexible inner tubular member 14. The aspiration port 38 may have various configurations and may be disposed at various locations on the inner tubular member 14. The cutting configuration 36 may comprise a cutting edge circumscribing the aspiration port 38 as depicted for flexible inner tube member 14. In particular, the cutting configuration 36 illustrated for flexible inner tubular member 14 comprises a peripheral cutting edge circumscribing the aspiration port 30 and comprising a series of cutting teeth on opposite sides of axis 33. In the case of angled tissue cutting instrument 10, the cutting configuration 36 of the inner tubular member 14 cooperates with the cutting edge 23 of the outer tubular member 12 to cut anatomical tissue. However, it should be appreciated that the cutting configuration 36 of the inner tubular member 14 can cut anatomical tissue independently, without there being a cooperating cutting edge on the outer tubular member 12.

The outer and inner member hubs 20 and 34 are ordinarily coupled with a powered surgical handpiece (not shown) for rotating the inner tubular member 14 relative to and within the outer tubular member 12. The powered surgical handpiece maintains the longitudinal position of the outer and inner members 12 and 14 relative to one another so that the cutting configuration 36 is exposed by or from the cutting port 22 to access and cut anatomical tissue as the inner tubular member 14 is rotated within the outer tubular member 12. A representative powered surgical handpiece is disclosed in U.S. Pat. No. 5,916,231 to Bays, the entire disclosure of which is incorporated herein by reference. As described above, the outer member 12 may have a cutting edge 23 that cooperates with the cutting configuration 36 to effect tissue cutting. There is sufficient annular space between the inner diameter of outer member 12 and the outer diameter of inner member 14 to define an irrigation channel between the outer and inner members for the flow of irrigating fluid supplied to the lumen of the outer member 12 through connector 24.

In order to access anatomical tissue in a cutting procedure, the angled tissue cutting instrument 10 is typically introduced through a natural or surgically created anatomical opening or passage in a patient's body to position the distal end 16 of the outer tubular member 12 at a cutting site in the patient's body while the handpiece is maintained externally of the patient's body. Exposure of the cutting configuration 36 by or from the cutting port 22 allows anatomical tissue at the cutting site to be accessed and cut by the cutting configuration. The aspiration port 38 establishes communication between the cutting site and the lumen or aspiration passage 40 of the flexible inner tubular member 14 and, when suction is produced in the lumen 40, typically via the handpiece, materials such as tissue debris are drawn into the lumen 40 via the aspiration port 38 for aspiration from the patient's body. Where the cutting configuration 36 comprises a cutting edge circumscribing the aspiration port 38, the cutting configuration and aspiration port register with the cutting port 22, and the cutting edge 23 if provided, as the inner member 14 rotates within the outer member 12. Irrigating fluid may be supplied to the irrigation channel between the outer and inner tubular members 12 and 14 for discharge at the cutting site through the cutting port 22. A source of irrigating fluid may be coupled with the connector 24 to supply the irrigating fluid to the lumen of outer member 12 for flow between the inner diameter of the outer tubular member 12 and the outer diameter of the flexible inner tubular member 14.

The flexible inner tubular member 14 has one or more flexible regions 42 for transmitting torque to rotate the cutting configuration 36 when the inner member 14 is rotated relative to and within the outer member 12 in forward and reverse rotational directions, while allowing the inner tubular member 14 to conform to the angled configuration of the outer tubular member 12 as it is rotated therein. The flexible inner tubular member 14 has one flexible region 42 of sufficient length to extend within the bend 26 so that the inner tubular member 14 conforms to the bend 26 while being rotatable within the outer tubular member 12. Accordingly, the flexible region 42 is disposed at a location along the length of the inner tubular member 14 in correspondence with the bend 26 in the outer tubular member 12.

FIGS. 2-7 illustrate the flexible inner tubular member 14 as well as a method of fabricating the flexible inner tubular member 14. As shown in FIG. 2, the flexible inner tubular member 14 comprises an elongate inner tube 44, which may be made of stainless steel, presenting an elongate tubular body 45 extending between distal end 30 and proximal end 32. The proximal end 32 of the inner tubular member 14 may be defined by a rearward or proximal end of the inner tube 44. The inner tube 44 may be knurled along the proximal end 32 to facilitate attachment of the inner tube 44 to the inner member hub 34. The distal end 30 of the flexible inner tubular member 14 may be made of stainless steel and may be formed integrally, unitarily or monolithically with the inner tube 44 or as a separate component attached to a forward or distal end of the elongate body 45 of inner tube 44. The lumen 40 of the inner tube 44 defines the aspiration passage of the flexible inner tubular member 14. The distal end 30 may comprise a cutting tip, which may be hollow to establish communication between the aspiration port 38 and the lumen 40 through inner tube 44. The inner tube 44 is longitudinally or axially straight and is of unbroken solid wall construction along the body 45, and at least along the flexible region 42. flexible inner tubular member 14 comprises an elongate inner tube 44, which may be made of stainless steel, presenting an elongate tubular body 45 extending between distal end 30 and proximal end 32. The proximal end 32 of the inner tubular member 14 may be defined by a rearward or proximal end of the inner tube 44. The inner tube 44 may be knurled along the proximal end 32 to facilitate attachment of the inner tube 44 to the inner member hub 34. The distal end 30 of the flexible inner tubular member 14 may be made of stainless steel and may be formed integrally, unitarily or monolithically with the inner tube 44 or as a separate component attached to a forward or distal end of the elongate body 45 of inner tube 44. The lumen 40 of the inner tube 44 defines the aspiration passage of the flexible inner tubular member 14. The distal end 30 may comprise a cutting tip, which may be hollow to establish communication between the aspiration port 38 and the lumen 40 through inner tube 44. The inner tube 44 is longitudinally or axially straight and is of unbroken solid wall construction along the body 45, and at least along the flexible region 42.

As shown in FIG. 3, a continuous helical cut 46 is formed in the body 45 of inner tube 44 along a length portion of the body 45 corresponding to the flexible region 42. The helical cut 46 is continuous from end to end and is formed in the inner tube 44 at a helix angle A in a first direction, i.e. clockwise (right hand) or counterclockwise (left hand), about the central longitudinal axis 33 of the inner tube 44 as depicted in FIGS. 3 and 4.

The helical cut 46 is formed in the inner tube 44 in a stepped pattern, best shown in FIG. 4, comprising repeating interconnected steps 48. However, the helical cut 46 can be formed in various other patterns including a plain helix or spiral without any steps. Each step 48 includes a transverse or circumferential cut segment 50 extending transverse to the length of the inner tube 44 and its body 45 in the first direction about the axis 33 of the inner tube 44 and its body 45, and a longitudinal cut segment 52 extending along the length of the inner tube 44 and its body 45 from the transverse cut segment 50 to the transverse cut segment 50 of the next step. The transverse cut segment 50 extends in the first direction about axis 33 at the helix angle A to a plane P perpendicular to the central longitudinal axis 33. The transverse cut segment 50 and the longitudinal cut segment 52 of the step 48 meet at an outside corner 54 to form a step configuration. The longitudinal cut segment 52 extends from the transverse cut segment 50 at the outside corner 54 to meet the transverse cut segment 50 of the next step at an inside corner 56. The transverse cut segment 50 meets the longitudinal cut segment of the previous step at the previous inside corner. The helical cut 46 may be of uniform pitch along the length portion as shown in FIG. 3, or may be of non-uniform pitch along the length portion to vary the flexibility of the inner tube 44 along the length portion.

Each transverse cut segment 50 defines the helix angle A with a plane P perpendicular to the central longitudinal axis 33 of the inner tube 44. The longitudinal cut segments 52 are shorter in length than the transverse cut segments 50, and the longitudinal cut segments 52 may be parallel to the central longitudinal axis 33. The steps 48 repeat at about 120° rotational intervals about the central longitudinal axis 33, with the outside corner 54 rotationally offset about 120° about axis 33 from the inside corner 56 of the previous step. In a preferred embodiment, the helix angle A is about 20° in a left hand first direction. However, the helical cut 46 may extend in the right hand direction, and the helix angle A can be other than about 20° in the left or right hand directions. Preferably, the helical cut 46 is formed in the inner tube 44 by laser cutting. The helical cut 46 may extend all the way to the cutting tip of the flexible inner tubular member to impart flexibility to the inner tube 44 adjacent the cutting tip. The helical cut 46 extends entirely through the wall thickness of inner tube 44 to impart flexibility while the inner tube remains materially and structurally interconnected.

As illustrated in FIG. 5, the flexible inner tubular member 14 further comprises a coating or layer of adhesive 58 disposed over the outer surface of the elongate body 45 of inner tube 44 along the helically cut length portion thereof corresponding to flexible region 42. The coating or layer of adhesive 58 may be applied to the outer surface of inner tube 44 in various ways including spraying the adhesive on the outer surface of the inner tube. Representative but not limiting adhesives include 3M Hi-Strength 90 spray adhesive and 3M High-Tack 76 spray adhesive. As shown in FIG. 5, a mandrel 60 may be disposed within the lumen 40 of the inner tube 44 with a close fit and of sufficient length to extend within the helically cut length portion and prevent the adhesive 58 from entering the lumen 40 through the helical cut 46.

FIG. 6 depicts a heat shrinkable sleeve 62 positioned or disposed over the adhesively coated and helically cut length portion of the inner tube 44. The sleeve 62 has an inner diameter receiving the outer diameter of the adhesively coated and helically cut length portion of inner tube 44 with a loose fit to facilitate sliding the sleeve 62 into position on the adhesively coated and helically cut length portion of the inner tube 44 corresponding to flexible region 42. FEP (fluorinated ethylene propylene) shrink tubing may be used as the sleeve 62. Other materials which may be suitable for sleeve 62 include polyester and polyolefin as well as other heat shrinkable materials. The sleeve 62 may have a wall thickness of about 0.010 inch and may have any suitable shrink ratio to obtain a close or snug fit over the inner tube 44 in response to the application of heat as described below. As an example, the sleeve 62 may have a 1.3 to 1 shrink ratio.

FIG. 7 depicts heat being applied to the sleeve 62 to shrink the sleeve diametrically to obtain a close or snug fit with the outer surface of inner tube 44 along the length portion. Heat can be applied in various ways including the use of induction heaters and heat guns. The heat shrunk sleeve 62 sandwiches the adhesive 58 between the outer surface of the inner tube 44 and the inner diameter of the sleeve 62, and the mandrel 60 may be used to prevent the adhesive from entering lumen 40 through helical cut 46. The adhesive 58 is bonded to the inner tube 44 and the sleeve 62. The flexible region 42 of the flexible inner tubular member 14 thusly comprises the helically cut length portion of inner tube 44 corresponding to flexible region 42, and a continuous solid flexible surface secured to the outer surface of the elongate body 45 along the helically cut length portion. The flexible surface may comprise sleeve 62, and the flexible surface may be secured to the outer surface of the inner tube 44 via the layer of adhesive 58 disposed between the flexible surface and the outer surface of the inner tube.

The flexible region 42 is capable of transmitting torque to rotate the cutting configuration 36 when the flexible inner tubular member 14 is disposed within the outer tubular member 12 while allowing the flexible inner tubular member 14 to conform to the angled configuration of the outer tubular member 12 as it is rotated therein. The flexible region 42 is capable of transmitting torque when the flexible inner tubular member 14 is rotated relative to and within the angled outer tubular member 12 in both forward and reverse rotational directions. The bond between adhesive 58 and the inner tube 44 and the sleeve 62 reduces wind-up of the flexible inner tubular member 14 in that clockwise and counterclockwise movements are restricted. Also, the heat shrunk sleeve 62 prevents the inner tube 44 from unwinding. The heat shrunk sleeve 62 is disposed over the entire helically cut length portion of the inner tube 44 and is bonded to the inner tube 44 such that the flexible region 42 replicates a solid wall tube construction in that no spaces or openings are presented along the outer surface of the flexible region 42. The wall thickness of the flexible region 42 comprises the wall thickness of the helically cut length portion of inner tube 44, the nominal thickness of adhesive 58 and the wall thickness of heat shrunk sleeve 62. Thus, the flexible region 42 comprises an inner wall, corresponding to the helically cut length portion of inner tube 44, along the inner diameter of the inner tubular member 14, and an outer wall, corresponding to solid surface 62 covering the helically cut length portion, along an outer diameter of the flexible inner tubular member 14. The wall thickness of the flexible region 42 is solid along its outer surface or diameter due to the solidity of the outer wall corresponding to solid surface or sleeve 62. Since there are no openings or spaces which go entirely through the wall thickness of flexible region 42 and since there are no openings or spaces along the outer surface or diameter of flexible region 42 which are in communication with the lumen 40, suction produced in the lumen or aspiration passage 40 is not lost through the wall thickness of the flexible region 42. Furthermore, irrigating fluid supplied between the angled outer tubular member 12 and the flexible inner tubular member 14 is not drawn into the lumen 40 along the flexible region 42 and body 45 of the inner tube 44 since there are no openings or spaces through the entire wall thickness of the flexible region 42 by which the irrigating fluid may enter the lumen 40. Aspiration efficiency is thusly increased in the angled tissue cutting instrument 10 in that the suction force in the aspiration passage 40 is more effectively applied at the aspiration port 38 without loss of suction along the body 45 of the flexible inner tubular member 14. Irrigation efficiency is also increased in the angled tissue cutting instrument 10 since irrigating fluid flowing in the irrigation channel between the outer and inner members 12 and 14 is more effectively discharged from the cutting port 22 since irrigating fluid is not lost along the body 45 of the flexible inner tubular member by being drawn into the lumen 40. The flexible inner tubular member 14 and, therefore, the angled tissue cutting instrument 10, can be fabricated at lower cost due to savings in materials and labor over prior flexible inner tubular members for angled tissue cutting instruments.

An alternative angled tissue cutting instrument is illustrated in FIG. 8 at 110. Angled tissue cutting instrument 110 is similar to angled tissue cutting instrument 10 except that angled outer tubular member 112 for angled tissue cutting instrument 110 has two bends 126 and flexible inner tubular member 114 of angled tissue cutting instrument 110 has two flexible regions 142 in correspondence with the bends 126, respectively. The bends 126 may have the same or different angles and/or radii of curvature and may extend in the same or different directions at various locations along the outer tubular member 112. In the angled tissue cutting instrument 110, the proximal bend 126A has a greater angle and a greater radius of curvature than the angle and radius of curvature of the distal bend 126B. Looking at FIG. 8, the proximal bend 126A extends downwardly while the distal bend 126B extends upwardly in the plane of axis 119. However, it should be appreciated that the bends 126A, 126B can extend upwardly, downwardly, or laterally and do not have to be contained in the same plane.

Flexible inner tubular member 114 comprises proximal flexible region 142A and distal flexible region 142B corresponding to the proximal and distal bends 126A and 126B, respectively. Each flexible region of the inner tubular member 114 is constructed in the same manner as the flexible region 42 and comprises a helically cut length portion of the inner tube 144 corresponding to the flexible region, a layer or coating of adhesive along the helically cut length portion of the inner tube 144, and a heat shrunk sleeve 162 diametrically shrunk over the adhesively coated helically cut length portion. The flexible inner tubular member 114 is rotatably disposed within the angled outer tubular member 112 with the flexible regions 142A and 142B disposed within the bends 126A and 126B, respectively, to transmit torque to the cutting configuration 136 when the flexible inner tubular member 114 is rotated within the angled outer tubular member 112, and the flexible regions 142A, 142B allow the inner tubular member 114 to confirm to the angled configuration of the outer tubular member 112 as it is rotated therein.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An angled tissue cutting instrument comprising
   an elongate angled outer tubular member comprising a distal end, a proximal end, a bend between said distal end and said proximal end, and an opening at said distal end defining a cutting port; and
   an elongate flexible inner tubular member rotatably disposed in said outer tubular member and comprising a distal end, a proximal end, an elongate tubular body between said distal end of said inner tubular member and said proximal end of said inner tubular member, a cutting configuration at said distal end of said inner tubular member for exposure by said cutting port to cut anatomical tissue when said inner tubular member is rotated within said outer tubular member, a flexible region along said body disposed in said bend, said flexible region comprising a continuous helical cut formed along a length portion of said body, a coating of adhesive disposed over an outer surface of said body along said length portion, and a heat shrunk sleeve disposed over said length portion with a close diametric fit, with said adhesive bonding said sleeve to said outer surface of said body along said length portion, said flexible region conforming to said bend while transmitting torque to rotate said cutting configuration when said proximal end of said inner tubular member is rotated in forward and reverse rotational directions, said sleeve bonded to said body providing resistance to wind-up and unwinding of said length portion when transmitting torque.

2. The angled tissue cutting instrument recited in claim 1 wherein said helical cut is formed through the wall thickness of said body at a helix angle in a first direction about a central longitudinal axis of said flexible inner tubular member.

3. The angled tissue cutting instrument recited in claim 2 wherein said helix angle is about 20° and said first direction is a left hand direction about said central longitudinal axis of said inner tubular member.

4. The angled tissue cutting instrument recited in claim 2 wherein said helical cut is formed in a stepped pattern comprising repeating interconnected steps.

5. The angled tissue cutting instrument recited in claim 4 wherein each step repeats at rotational intervals of about 120° about said central longitudinal axis of said inner tubular member.

6. The angled tissue cutting instrument recited in claim 4 wherein each of said steps comprises a transverse cut segment extending transverse to the length of said body at said helix angle to a plane perpendicular to said central longitudinal axis of said inner tubular member and a longitudinal cut segment extending from said transverse cut segment along the length of said body.

7. The angled tissue cutting instrument recited in claim 1 wherein said adhesive comprises a spray adhesive.

8. The angled tissue cutting instrument recited in claim 1 wherein said sleeve is made of fluorinated ethylene propylene.

9. The angled tissue cutting instrument recited in claim 8 wherein said sleeve has a thickness of about 0.010 inch and a shrink ratio of about 1.3 to 1.

10. An angled tissue cutting instrument comprising
an elongate angled outer tubular member comprising a distal end, a proximal end, a bend between said distal end and said proximal end, and an opening in said distal end defining a cutting port; and
an elongate flexible inner tubular member rotatably disposed in said outer tubular member and comprising a distal end, a proximal end, an elongate tubular body between said distal end and said proximal end of said inner tubular member, a cutting configuration at said distal end of said inner tubular member for exposure by said cutting port to cut anatomical tissue when said inner tubular member is rotated within said outer tubular member, and a flexible region along said body disposed within said bend, said flexible region comprising an outer wall along an outer diameter surface of said inner tubular member and an inner wall along an inner diameter surface of said inner tubular member, said outer wall being secured to said inner wall, said inner wall comprising a helically cut length portion of said body having a cut through the inner wall thickness of said body extending helically along said length portion, said outer wall comprising a continuous solid flexible surface covering said helically cut length portion, said flexible region conforming to said bend while transmitting torque to rotate said cutting configuration when said proximal end of said inner tubular member is rotated in forward and reverse rotational directions, said outer wall secured to said inner wall providing resistance to wind-up and unwinding of said helically cut length portion.

11. The angled tissue cutting instrument recited in claim 10 wherein said flexible surface is adhesively secured to an outer surface of said body.

12. The angled tissue cutting instrument recited in claim 10 wherein said flexible surface comprises a heat shrunk sleeve receiving said helically cut length portion therein.

13. The angled tissue cutting instrument recited in claim 10 wherein said cut is formed through said inner wall thickness of said body in a stepped pattern.

14. The angled tissue cutting instrument recited in claim 10 wherein said outer tubular member has a lumen receiving said inner tubular member and further comprising an aspiration port in said distal end of said inner tubular member and an aspiration passage through said body in communication with said aspiration port, wherein said flexible surface prevents communication between said aspiration passage and said lumen along said flexible region.

15. The angled tissue cutting instrument recited in claim 10 wherein said outer tubular member has a lumen in communication with said cutting port, said inner tubular member is received in said lumen, said lumen defines an irrigation channel for receiving irrigating fluid between said outer tubular member and said inner tubular member for discharge through said cutting port, said body has a lumen, wherein said flexible surface prevents communication between said lumen of said body and said irrigation channel along said flexible region.

16. The angled tissue cutting instrument recited in claim 10 wherein said outer tubular member includes a plurality of said bends and said inner tubular member includes a plurality of said flexible regions disposed within said bends, respectively.

* * * * *